United States Patent [19]

Brown

[11] Patent Number: 5,781,932
[45] Date of Patent: Jul. 21, 1998

[54] FOREHEAD PERSPIRATION COLLECTOR/DISCHARGER

[76] Inventor: Robert L. Brown, 4800 W. Anton Rd., Tucson, Ariz. 85746

[21] Appl. No.: 862,604

[22] Filed: May 23, 1997

Related U.S. Application Data

[63] Continuation-in-part of Ser. No. 697,479, Aug. 26, 1996, which is a continuation-in-part of Ser. No. 565,831, Dec. 1, 1995, abandoned.

[51] Int. Cl.$^6$ .................................................. A41D 20/00
[52] U.S. Cl. ............................ 2/181; 2/181.6; 2/DIG. 11
[58] Field of Search .......................... 2/181, 181.2, 181.4, 2/181.6, 181.8, 182.8, 174, DIG. 11, 171.2, 171.3, 7, 425, 171; 604/312, 19

[56] References Cited

U.S. PATENT DOCUMENTS

| 1,084,596 | 1/1914 | Alexander | 2/181 |
|---|---|---|---|
| 1,750,937 | 3/1930 | Morgan | 2/174 |
| 2,320,782 | 6/1943 | Larsen | 2/171 |
| 3,319,262 | 5/1967 | Lee | 2/174 |
| 4,130,902 | 12/1978 | Mackenroth, III et al. | 2/171.2 |
| 4,393,519 | 7/1983 | Nicastro | 2/12 |
| 4,616,367 | 10/1986 | Jean | 2/452 |
| 4,621,378 | 11/1986 | Hatchman | 2/9 |
| 4,626,247 | 12/1986 | Frankel | 2/181.8 |
| 4,638,512 | 1/1987 | Frankel | 2/DIG. 11 |
| 4,742,581 | 5/1988 | Rosenthal | 2/181 |
| 4,856,116 | 8/1989 | Sullivan | 2/DIG. 11 |
| 4,885,808 | 12/1989 | Carpenter | 2/452 |
| 4,951,316 | 8/1990 | Moody | 2/12 |
| 4,955,087 | 9/1990 | Perez | 2/12 |
| 5,007,109 | 4/1991 | Wheeler | 2/10 |
| 5,054,122 | 10/1991 | Sher | 2/181.6 |
| 5,056,163 | 10/1991 | Chou | 2/181 |
| 5,105,475 | 4/1992 | Lynd | 2/10 |
| 5,105,476 | 4/1992 | Cox | 2/12 |
| 5,146,630 | 9/1992 | Richard | 2/DIG. 11 |
| 5,309,577 | 5/1994 | Buononato | 2/452 |
| 5,572,745 | 11/1996 | Mainus | 2/DIG. 11 |

Primary Examiner—Amy B. Vanatta

[57] ABSTRACT

A forehead perspiration collector and discharger constructed primarily of various sizes of vinyl or rubber tubing. The larger sized tube of the device having absorption apertures rests upon the wearer's forehead for taking in perspired fluids whereby the smaller tubes direct any contained excess fluids out to the rear discharge site. An elastic cord is joined to sliding cord retainers which rides over the tubular sides of the device which serves as an adjustable enclosure for securing to a wearer's head.

2 Claims, 2 Drawing Sheets

FOREHEAD PERSPIRATION COLLECTOR/ DISCHARGER

This application is a continuation-in-part of U.S. Ser. No. 08/697,479, filed Aug. 26, 1996, now U.S. Pat. No. 5,740,556, which is a continuation-in-part of U.S. Ser. No. 08/565,831, filed Dec 1, 1995, now abandoned.

BACKGROUND OF THE PRESENT INVENTION

This invention relates to sweat bands and articles of such that capture flowing forehead perspiration for the purpose of alleviating sweaty run off over the facial area. It is common knowledge how irritating sweat is to the human eye. Consequently a number of devices have been created to confront the problem and are usually constructed of soft spongy or cloth materials that are a directly absorbable material being permeable in composition. This invention however uses impermeable materials to collect and discharge such annoying fluids.

BACKGROUND-DESCRIPTION OF PRIOR ART

Throughout the world each day somewhere thousands of people are engaged in some activity that cause them to sweat profusely. Whether hard at work or fast at play people are desirous of something new that would be more simply effective, attractive and require less or no maintenance over what is currently available. What is presently available are all the familiar variety of sweat bands constructed of the usual materials that have absorbing qualities, but don't fully address any new technologies confronting sweat absorption.

One such article illustrates a common form of an absorbent sweatband consisting of a cotton material that encircles the head and is designed around rigid conventional style glasses. Cloth sweat bands must be periodically laundered to maintain an acceptable degree of sanitation.

Another type of device consists only of a heavy absorption sweat band consisting of traditional liquid absorbing qualities typical of cloths and fabrics that come in close contact with the forehead secured by velcro.

Another apparatus appears to be a device designed for face protection from airborne flying debris as well as including a moisture absorbing sweat band. It is similar to other examples in its art category and requires the same maintenance applications for a sanitary use. The effectiveness of traditional sweat bands is dependant upon the time and rate it will absorb until saturation is reached. This article does not appear to offer any satisfaction in aesthetics and may be to cumbersome to find a convenient place to carry handily.

Another device illustrates a plastic headband with a fabric sweatband and comprises a movable shaded lens that may serve as a visor in the up position or a lens in the down position. It appears more compact than other described relative art specimens but again utilizes common sweat absorbing materials designed to come into direct contact with the forehead skin as if to mop up flowing moisture.

There are other examples of references but they all essentially work under the same principle and would be to repetitive to mention.

SUMMARY OF THE INVENTION

This invention is comprised basically of a few sizes of common tubing, a piece of elastic cord and a small piece of absorbent material. The complete embodiment is effective at confining flowing forehead perspiration within tubes. This allows said liquids to retain there free fluid state so gravitational forces will facilitate there immediate movement through discharge tubing. In summary this simple device utilizes collection and discharge to confront the annoying problem of flowing forehead perspiration.

OPERATION OF THE INVENTION

This invention will be ready for use after the wearer has placed the larger forehead perspiration absorption section across the lower forehead, with the absorbing apertures facing up and toward the forehead, and has slid the cord retainers forward for a comfortably snug fit. The largest tube in diameter is the forehead perspiration absorption section bearing cutouts or apertures for allowing flowing forehead perspiration to be collected and contained within its inner canal. Each end of the fluid absorption section has junction with a smaller diameter tube which are the drain tubes and are each attached to the forehead section by a connective joining tube. The rearward ends of these drain tubes terminate around the back of the wearers head where they have junction with a length of a tubular discharge coupler which can have inserted an absorbent material such as sponge. Generally it is recommended that no adhesives or glues be used here so the drain tubes can be removed or inserted at will from the discharge coupler for the insertion of absorption materials if so desired. Also since this device would normally be carried around ones neck when not in use it would be desirable for it to readily come apart if a sudden tensional force were to be accidentally applied to it. This discharge coupler also bears apertures or cutouts for the discharge of sweaty fluids. The sponge if so utilized serves to prevent an immediate and constant flow of sweaty discharged fluids for those who are sensitive to their backside becoming wet. This tube also functions essentially as an aerated capsule to assist in some evaporation potential depending on atmospheric humidity levels. The device is secured to the wearers head by means of an elastic cord fastened to cord retainers that slide along the drain tubes surface.

Therefore considering the aforementioned descriptions flowing forehead perspiration enters the forehead section through its absorption apertures and becomes trapped within the forehead section's canal. When perspiring sufficiently these fluids will collect until enough volume will allow itself to rise and flow out through the canals of the drain tubes that have junction with the aft located discharge coupler's release apertures or cutouts. Since this device is a complete enclosure as an added convenience it is easily carried around one's neck.

OBJECTS AND ADVANTAGES

The object of this invention is to maximize appeal and cost efficiency within a new technology at forehead absorption that would be acceptable for either sex or user type.

Another object of my invention is to invent an effective absorption, collection and discharge system within a device that focuses on size, weight, number and aesthetics of its parts and self.

Another object of my invention is to create an absorption, collection and discharge system that confines its discharged effluent through a series of cutouts or apertures in a singular location within the device behind the head.

Another object of my invention is to produce a technologically advanced type of sweat band that can be manufactured from ready available materials.

Another object of my invention is to create an advanced form of sweat band that is easily adaptable to any size of head within its generous full enclosure.

3

Another object of my invention is to create an advanced sweat band that addresses a convenience of accessibility by wearing it around the neck when not in use.

Another object of my invention is in offering the site of effluent discharge an option of a terminal absorption process utilizing an absorbent material to delay immediate discharge if so desired.

DESCRIPTION OF DRAWING FIGURES

Figure 1:
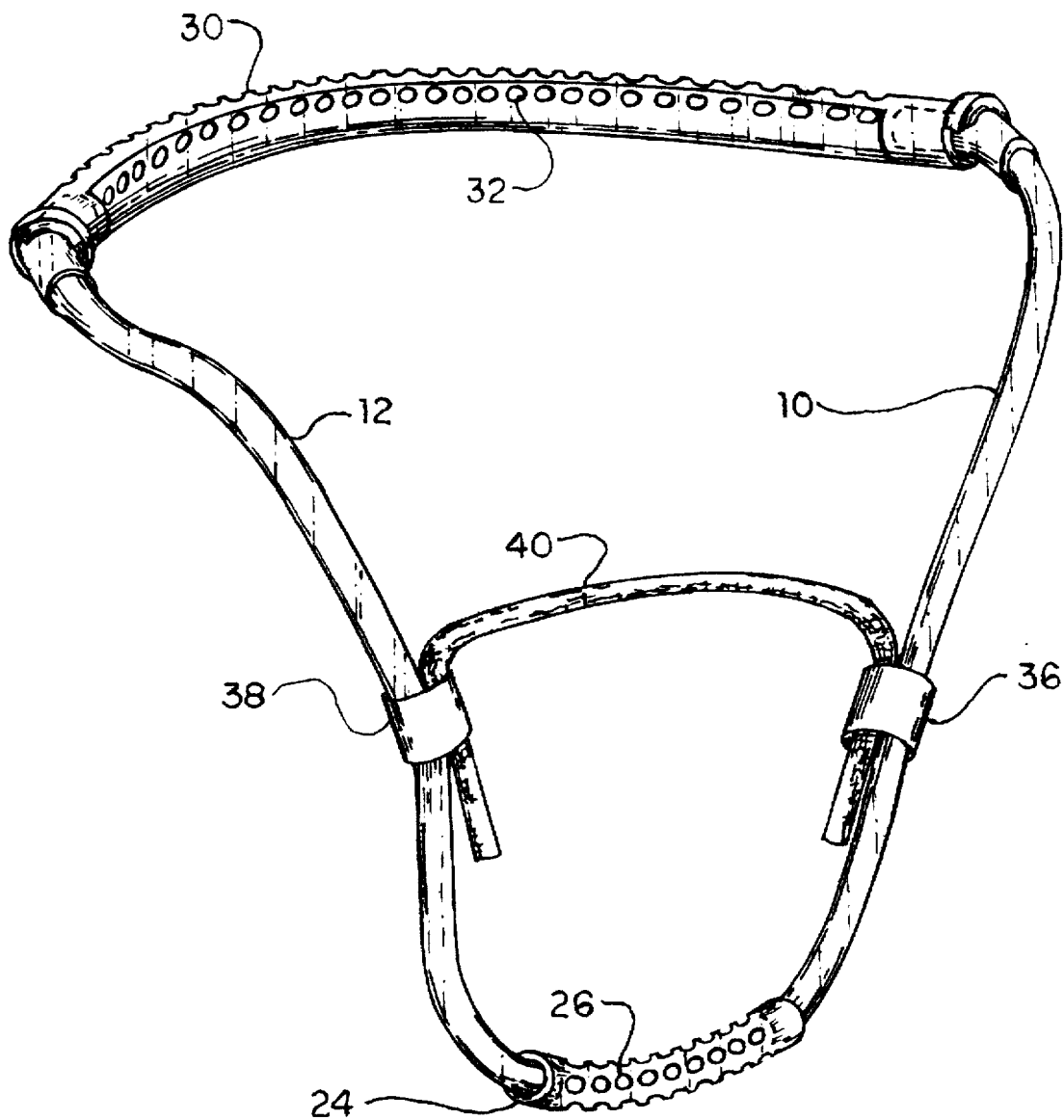
FIG. 1 shows the complete article in assembly.

DRAWING REFERENCE NUMERALS
10: right side drain tube
12: left side drain tube
14: internal canal of absorbing forehead section
16: right side trough seal
18: left side trough seal
20: right side tube connector
22: left side tube connector
24: discharge coupler
26: discharge coupler apertures
28: absorbent material
30: forehead perspiration absorption section
32: forehead section fluid collecting apertures
34: colored liner body pad
36: right side sliding cord retainer
38: left side sliding cord retainer
40: elastic cord

DESCRIPTION OF THE INVENTION

Referring now to the drawings, FIG. 1 shows the complete assembled device. Tube 30, having absorbing apertures 32, and or cutouts will serve as the means for fluid collection from the fore head when the article is properly fitted. The tube's general measurements though not limited to will be approximately nine and one half inches in length and have an external diameter of one half inch and an internal diameter of three eights of an inch. Forehead perspiration absorption tube 30, bears a thinly embodied covering 34 that will serve as a resting surface for the forehead and may consider comfort as well as exhibit a number of chosen colors for attraction. Generally the first row of absorbing apertures will rest along this thin covering's longitudinal surface and begin and end within an inch of its host tube's extremities. All the absorbing apertures 32, are located on the upper quadrants of tube 30. To the ends of tube 30 is then inserted a joining connector tube right side 20, and left side 22, both being about one inch in length and having an external diameter to be fitted there and also having an internal diameter appropriately sized for their reciprocal counterparts, drain tubes 10 and 12. To the outer surface of the connecter tubes 20 and 22 and against the ends of absorbing tube 30 is embodied sectional seals 16 and 18 which serves to dam any flowing fluids moving along the absorption trough between the wearer's forehead and absorption tube 30. Next discharge coupler tube 24 being about three inches in length bearing drain apertures 26 and having an internal diameter of about one quarter inch is fitted over each end of the drain tubes 10 and 12. These drain tubes should be of such a length that when connected to the forehead perspiration absorption tube 30 and to the discharge coupler tube 24, the device will be large enough to fit most head sizes. Therefore the total unassembled length of the drain tubes would have a seven to nine inch range. Next sliding cord retainers 36 and 38 having channels extending

Figure 2:
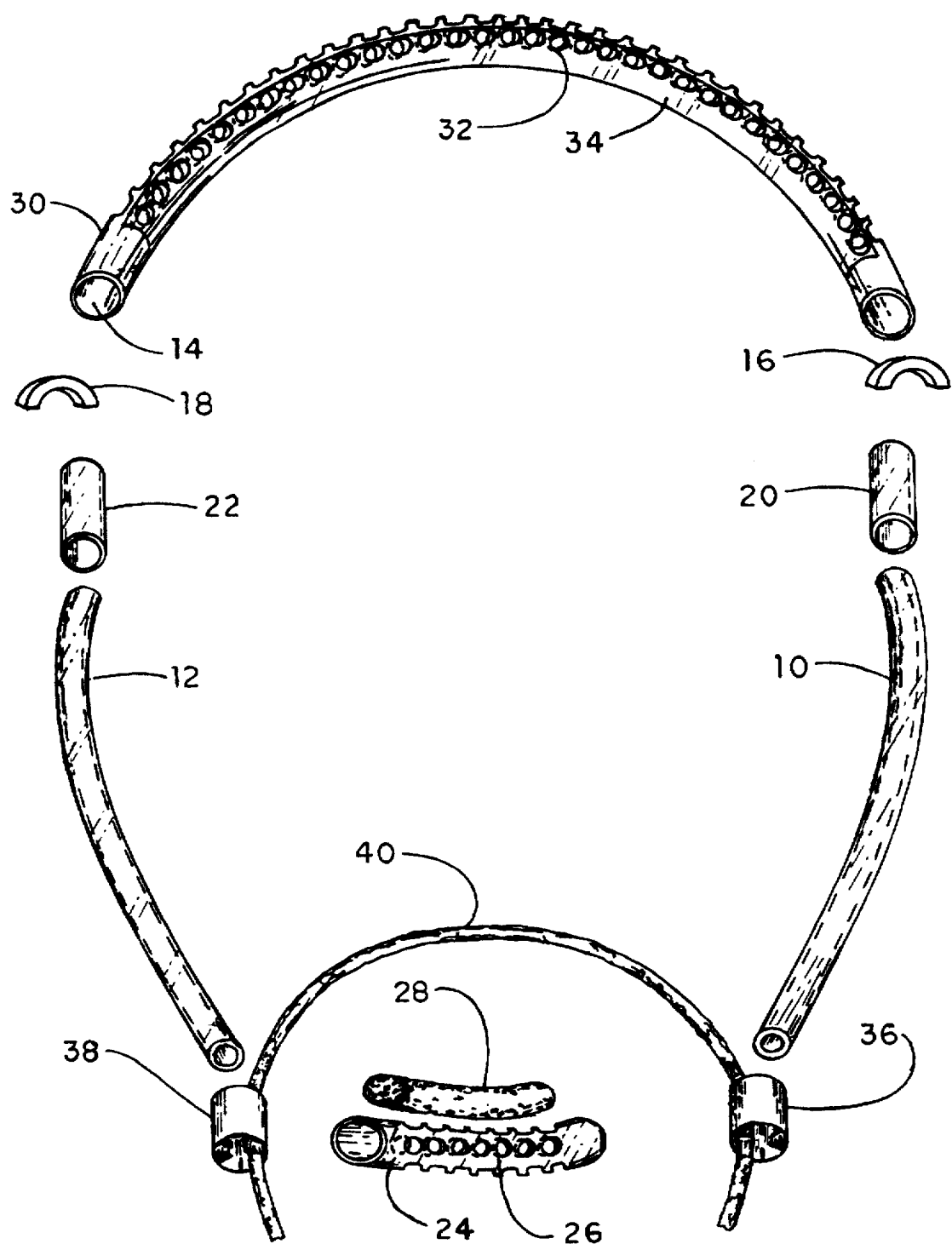
FIG. 2 shows a detailed view of the assemblies parts.

4 around its internal diameter each have an end of elastic cord 40 placed and seated within one of the channel grooves. Cord retainers 36 and 38 are now placed over and slid down along drain tubes 10 and 12. These cord retainers are the means for attaching the device to the head, by sliding them forward the enclosing head size becomes smaller. Sliding them rearward enlarges the head size. Next drain tubes 10 and 12 are inserted into the canals of connectors 20 and 22 completing the assembly process. The drain ends of tubes 10 and 12 that fit into the discharge coupler 24, may be removed or inserted at any time to install absorbent material 28 if so desired. FIG. 2 shows a more detailed view of each part in an exploded format. Clear vinyl hose not unlike those used in aquariums seems to work very well but other types of hose materials could be used that have similar or improved properties. This forehead section is designed to absorb fluids through wall voids and contain such fluids in a free state so that these fluids may flow freely out so its important that at least a portion of the selected materials be impermeable in substance. Therefore in summary flowing forehead perspiration is collected through the absorbing apertures 32, of tube 30 and then flows through its canal 14 to the canal origins of the joining connector tubes 20 and 22 where drain tubes 10 and 12 have junction. All effluent then flows through and along the drain tubes until it enters the discharge coupler tube 24, where it will flow freely out through its discharge apertures 26, provided material 28 has been omitted. In this example adhesives or glues are not necessary for the assembly process. It is important that the tubular materials be flexibly endurable and comfortably resilient for wearing comfort.

SCOPE OF THE INVENTION

While the above description may seem accurately specific those skilled in the art will imagine other variants of its principles. They will incorporate similar units utilizing my absorption, collection and discharge principle to have points of discharge in front of the face instead of the rear or side. They will create exceptional form and sensational color with catchy names in attempt to differentiate it. They may manufacture a similar device that uses a construction where the lower half is impermeable in substance such as vinyl and the upper tubular half is porous material such as foam sponge. They will deliver it with wondrous packaging and advertising. They will incorporate and disincorporate into it. The reader is requested to determine the scope of the invention by the appended claims and their legal equivalents, and not by the examples which have been given.

What is claimed is:

1. A forehead sweat absorption device for collection and discharge of forehead perspiration including a means for adjustable attachment to the wearer's head, wherein said device functions by collecting and disposing of perspired fluids through a transfer process via tubing canals, said forehead sweat absorption device comprising a number of impermeable elements being substantially tubular and varying in size to include a forehead perspiration absorption section, a pair of drain tubes, a pair of joining tubes having a connective means, a discharge coupling tube and an absorbent element, wherein said means for adjustable attachment includes a means for securing to the head comprising a piece of elastic cord and a pair of annular shaped cord retainers, said pair of joining tubes each having a connective means to each end of said forehead perspiration absorption section further including a means to join each said joining tube to each said drain tube so that each said drain tube extends out of each end of said forehead perspiration absorption section, said pair of annular cord retainers each having a means for attachment to an end of said elastic cord and means for attachment to an end of said drain tube so that said cord retainers will slide forward or rearward over the length of each said drain tube such that said elastic cord forms an adjustable attachment means to a wearer's head and said forehead perspiration absorption section has a predetermined pattern of wall cutouts or apertures upon its upper quadrants for the purpose of fluid absorption, said forehead section having said apertures further comprising a means to seal off and collect flowing forehead perspiration coming into contact with said device while being worn on a wearer's head and further including a means to confine such fluids in containment until increasing quantities become gravitationally expelled through said drain and discharge tubes said forehead sweat absorption device comprising a single said discharge coupler tube having a pattern of apertures there around for fluid discharge, said coupler having a junction with rearward ends of said drain tubes so that fluid disposal is confined to one aft area through said discharge coupler, said forehead sweat absorption device being a continuous surrounding tubular structure for conveying fluids having a substantially oval configuration that comprises a fluid absorption process on a foreward structure and a fluid discharge process on a rearward structure, said impermeable elements of said forehead sweat absorption device comprising a series of fluid transfer tubes that are sized in proportion relative to one another to provide a more immediate and efficient fluid transfer process.

2. The forehead sweat absorption device as in claim 1 further comprising a piece of absorbent material disposed in said discharge coupler for preliminary retarding of fluid escape.

\* \* \* \* \*